(12) United States Patent
Kawa et al.

(10) Patent No.: US 8,758,734 B2
(45) Date of Patent: Jun. 24, 2014

(54) SUN PROTECTING EMULSION PROVIDED WITH A FOAM DISPENSER

(75) Inventors: Rolf Kawa, Monheim (DE); Peter Finkel, Odenthal (DE); Hannelore Merheim, Cologne (DE); Sylvia Henig, Leverkusen (DE)

(73) Assignee: Cognis IP Management GmbH, Duesseldorf (DE)

( * ) Notice: Subject to any disclaimer, the term of this patent is extended or adjusted under 35 U.S.C. 154(b) by 1696 days.

(21) Appl. No.: 10/511,633

(22) PCT Filed: Apr. 10, 2003

(86) PCT No.: PCT/EP03/03711
§ 371 (c)(1),
(2), (4) Date: May 6, 2005

(87) PCT Pub. No.: WO03/088941
PCT Pub. Date: Oct. 30, 2003

(65) Prior Publication Data
US 2005/0226824 A1    Oct. 13, 2005

(30) Foreign Application Priority Data
Apr. 19, 2002  (DE) .................................. 102 17 474

(51) Int. Cl.
| | |
|---|---|
| A61K 8/72 | (2006.01) |
| A61K 8/06 | (2006.01) |
| A61K 8/04 | (2006.01) |
| A61Q 5/00 | (2006.01) |
| A61Q 7/00 | (2006.01) |

(52) U.S. Cl.
CPC ............... A61K 8/064 (2013.01); A61K 8/046 (2013.01)
USPC ........................................ 424/70.11; 424/401

(58) Field of Classification Search
CPC ......... A61K 8/064; A61K 8/04; A61K 8/046; A61K 8/06; A61K 8/85
USPC .............................................. 424/401, 70.11
See application file for complete search history.

(56) References Cited

U.S. PATENT DOCUMENTS

| | | | |
|---|---|---|---|
| 4,305,936 A * | 12/1981 | Klein ............................. 514/174 |
| 5,705,169 A | 1/1998 | Stein et al. |
| 5,730,960 A | 3/1998 | Stein et al. |
| 5,840,943 A | 11/1998 | Ansmann et al. |
| 5,945,091 A | 8/1999 | Habeck et al. |
| 5,962,452 A | 10/1999 | Haase et al. |
| 5,989,527 A * | 11/1999 | Siegfried et al. ................ 424/59 |
| 6,193,960 B1 | 2/2001 | Metzger et al. |
| 6,207,140 B1 * | 3/2001 | Seipel et al. .................... 424/59 |
| 6,264,961 B1 * | 7/2001 | Ansmann et al. ............. 424/401 |
| 6,280,712 B1 | 8/2001 | Ansmann et al. |
| 6,340,662 B1 | 1/2002 | Millhoff et al. |
| 6,368,577 B1 | 4/2002 | Kropf et al. |
| 6,482,418 B1 * | 11/2002 | Loehl et al. ................... 424/401 |
| 6,576,678 B1 | 6/2003 | Bruening et al. |
| 2004/0105825 A1 | 6/2004 | Henning |

FOREIGN PATENT DOCUMENTS

| | | |
|---|---|---|
| DE | 197 12 033 A1 | 9/1998 |
| DE | 199 55 375 | 6/2001 |
| EP | 0 694 521 | 1/1996 |
| EP | 0 766 661 | 4/1997 |
| EP | 0 693 471 B1 | 1/1998 |
| EP | 0 818 450 B1 | 1/1998 |
| EP | 0 860 164 | 8/1998 |
| EP | 0 878 469 | 11/1998 |
| EP | 1 316 300 | 6/2003 |
| WO | WO 99 11235 | 3/1999 |
| WO | WO 99 67016 | 12/1999 |
| WO | WO 00 36063 | 6/2000 |
| WO | WO 00 78629 | 12/2000 |

OTHER PUBLICATIONS

Sememczuk et al., "Synergistic Sun System", Soap & Cosmetics, vol. 75, 1999, pp. 48; XP 002245496.
Airspray Int. B.V., Product Information; XP 002245495.
P. Finkel, "Formulierung kosmetischer Sonnenschutzmittel", SÖFW-Journal, 122, (1996), pp. 543-546 & 548.
P. Finkel, "Formulierung kosmetischer Sonnenschutzmittel", Parfumerie und Kosmetik, 80, No. 3 (1999), pp. 10-12, 14-16.
"Kosmetik-Verordnung", Appendix 6, Parts A and B, Deutsches Institut für Körperpflege und Hygiene e.V.

* cited by examiner

Primary Examiner — Fereydoun G Sajjadi
Assistant Examiner — Danielle Sullivan
(74) Attorney, Agent, or Firm — Servilla Whitney LLC (57) ABSTRACT

A system for dispensing a foamed aqueous emulsion is provided. The system is a foam-dispensing container and an aqueous emulsion of an oil component with improved foamability. The foamability is improved by including in the emulsion a polyol poly-12-hydroxystearate surfactant as an emulsifier. The aqueous emulsion contains polyol poly-12-hydroxystearate, an oil component, other surfactants and can contain UV protection factors, water and optionally other auxiliaries and additives.

11 Claims, 1 Drawing Sheet

SUN PROTECTING EMULSION PROVIDED WITH A FOAM DISPENSER

RELATED APPLICATIONS

This application is filed under 35 U.S.C. §371 claiming priority of PCT/EP Application Number 03/03711 filed Apr. 10, 2003; claiming priority from DE 102 17 474.1 filed Apr. 19, 2002, the entire contents of each application are incorporated herein by reference.

FIELD OF THE INVENTION

This invention relates to foamable cosmetic and/or pharmaceutical sun protection emulsions in a foam dispenser.

RELATED ART

Although emulsions have been known for some time, intensive efforts are constantly being made on the cosmetics market to improve the sensory properties in particular of these disperse systems because unfavorable rheological properties, such as rheopexy or example, make uniform application very difficult. At present, surfactant-containing emulsions foamed with air by a special pump mechanism are being marketed to an increasing extent. By virtue of the relatively low density of the foam, systems such as these can be spread over the skin more easily and uniformly. In practice, however, it has been found that the foam of such emulsions—as described, for example in DE 199 55 375 A1—lacks strength and intensity, collapses very quickly and leaves behind a watery, not altogether satisfactory sensory impression on the skin. The uniform and homogeneous spreading of these foams on the skin is not always guaranteed. However, for special applications, such as sun protection emulsions for example, uniform spreading is particularly important for obtaining a uniform and homogeneous distribution of the UV protection factors used over the skin and, hence, a reproducible sun protection effect.

Accordingly, the problem addressed by the present invention was to provide sun protection emulsions which could readily be foamed with a gas, particularly air, and which would form a stable foam that would spread easily and uniformly and would leave the skin with light sensory impression. Another problem addressed by the invention was to provide particularly dermatologically compatible foamable sun protection emulsions.

BRIEF DESCRIPTION OF THE INVENTION

It has surprisingly been found that sun protection emulsions based on polyol poly-12-hydroxystearates as emulsifier can be foamed particularly easily and form very stable and dermatologically compatible foams which enable the UV protection factors to be distributed very evenly.

Accordingly, the present invention relates to a system of a manually operated foam dispenser and a sun protection emulsion characterized by a content of:
(a) polyol poly-12-hydroxystearates
(b) oil components
(c) other surfactants
(d) UV protection factors and
(e) water.

The present invention also relates to the sun protection emulsions themselves. The foamable sun protection emulsion normally contains 30 to 80% by weight, preferably 50 to 80% by weight and more particularly 60 to 80% by weight water.

The sun protection emulsion stored in the foam dispenser preferably contains (a) 2 to 10% by weight polyol poly-12-hydroxystearates, (b) 1 to 20% by weight oil components, (c) 0.5 to 10% by weight surfactants and (d) 0.5 to 20% by weight UV protection factors and (d) 30 to 80% by weight water. In a preferred embodiment, the emulsion is a w/o sun protection emulsion. The present invention also relates to the use of polyol poly-12-hydroxystearates, more particularly poly(12-hydroxystearic acid)polyglycerol esters, for improving the foamability of emulsions in foam dispensers.

DETAILED DESCRIPTION OF THE INVENTION

Polyol Poly-12-hydroxystearates (Component a)

The polyol poly-12-hydroxystearates which form component (a) are known substances which are marketed by Cognis Deutschland GmbH, for example under the names of "Dehymuls® PGPH" and "Eumulgin® VL 75" (mixture with Coco Glucosides in a ratio by weight of 1:1) or Dehymuls® SBL. Particular reference is also made in this connection to European Patent EP 0 766 661 B1. The polyol component of these emulsifiers may be derived from substances which contain at least 2, preferably 3 to 12 and more preferably 3 to 8 hydroxyl groups and 2 to 12 carbon atoms. Typical examples are glycerol and polyglycerol;
alkylene glycols such as, for example, ethylene glycol, diethylene glycol, propylene glycol;
methylol compounds such as, in particular, trimethylol ethane, trimethylol propane, trimethylol butane, pentaerythritol and dipentaerythritol;
alkyl oligoglucosides containing 1 to 22, preferably 1 to 8 and more preferably 1 to 4 carbon atoms in the alkyl group such as, for example, methyl and butyl glucoside;
sugar alcohols containing 5 to 12 carbon atoms such as, for example, sorbitol or mannitol,
sugars containing 5 to 12 carbon atoms such as, for example, glucose or sucrose;
amino sugars such as, for example, glucamine.

Among the emulsifiers suitable for use in accordance with the invention, reaction products based on polyglycerol are particularly important by virtue of their excellent applicational properties. It has proved to be of particular advantage to use reaction products of poly-12-hydroxystearic acid with polyglycerols which have the following homolog distribution (the preferred ranges are shown in brackets):

| | |
|---|---|
| glycerols | 5 to 35 (15 to 30) % by weight |
| diglycerols | 15 to 40 (20 to 32) % by weight |
| triglycerols | 10 to 35 (15 to 25) % by weight |
| tetraglycerols | 5 to 20 (8 to 15) % by weight |
| pentaglycerols | 2 to 10 (3 to 8) % by weight |
| oligoglycerols | to 100 % by weight |

In a preferred embodiment of the invention, the polyol poly-12-hydroxystearate present is at least one poly(1 2-hydroxystearic acid)polyglycerol ester which is marketed, for example, by Cognis Deutschland GmbH & Co. KG under the name of Dehymuls® PGPH and which is a w/o emulsifier. This w/o emulsifier may normally be present in the sun protection emulsions according to the invention in a quantity of 0.5 to 10% by weight and is preferably present in a quantity of 2 to 10% by weight and more particularly in a quantity of 3 to 8% by weight.

Oil Components (Component b)

In the context of the invention, oil components which form component (b) are any substances or mixtures of substances suitable for cosmetic applications which are liquid at 20° C. and immiscible with water at 25° C. Depending on the application form (for example w/o or o/w emulsion) and the UV protection factors used (liquid or crystalline), the oil components may make up from 1 to 20% by weight of the composition as a whole. In the case of liquid UV protection factors, the lower limit may even be at 1% by weight. The oil components, which may be both pure substances and mixtures, are normally used in a quantity of 1 to 20% by weight, preferably in a quantity of 1 to 15% by weight and more particularly in a quantity of 5 to 10% by weight. According to the invention, a mixture of oil components is preferably used.

Suitable oil components are, for example, Guerbet alcohols based on fatty alcohols containing 6 to 18 and preferably 8 to 10 carbon atoms (for example Eutanol® G), esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{3-38}$ alkylhydroxycarboxylic acids with linear or branched $C_{6-22}$ fatty alcohols, more especially diethyl hexyl malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates such as, for example, Dicaprylyl Carbonate (Cetiol® CC), Guerbet carbonates based on fatty alcohols containing 6 to 18 and preferably 8 to 10 carbon atoms, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols (Hydagen® HSP, Sovermol® 750, Sovermol® 1102), silicone oils (cyclomethicone, silicon methicone types, etc.) and/or aliphatic or naphthenic hydrocarbons such as, for example, mineral oil, Vaseline, petrolatum, squalane, squalene, isohexadecanes or dialkyl cyclohexanes.

Foams with particularly elegant sensory properties are obtained where dialkyl ethers and/or dialkyl carbonates are (co)used as oil components. According to the invention, therefore, they represent preferred oil components. A particularly preferred combination of oil components contains triglycerides and dialkyl carbonates, preferably a mixture of Dicaprylyl Carbonate (Cetiol® CC) and Cocoglyceride (Myritol® 331) and/or Caprylic/Capric Triglyceride (Myritol® 318). In addition, it can be of advantage to use silicone compounds, such as cyclomethicone and dimethicone for example, in order to prevent the formation of unwanted so-called white residues (microfoam) on the skin.

Foams with particularly elegant sensory properties are also obtained with such oils as Cetiol® OE (Dicaprylyl Ether), Finsolv® TN ($C_{12/15}$ Alkyl Benzoate), Tegosoft® SP (Ethylhexyl Palmitate) and combinations of these oils.

Surfactants (Component c)

The composition according to the invention contains other surfactants that do not come under component (a) for the purpose of foam formation and stabilization. These surfactants are the surface-active substances known to the expert. The surfactants are present in the compositions according to the invention in quantities of 0.5 to 10% by weight, preferably 1 to 8% by weight and more particularly 2 to 6% by weight, based on the active substance. According to the invention, the surfactants may be used individually or, preferably, in the form of mixtures.

In principle, the compositions may contain anionic, amphoteric, zwitterionic, nonionic and, optionally, cationic surfactants. In a preferred embodiment, at least one surfactant selected from the group of anionic surfactants and/or zwitterionic surfactants is present. A combination of surfactants from these two classes is preferred (vide infra).

Anionic surfactants are characterized by a water-solubilizing anionic group, such as for example a carboxylate, sulfate, sulfonate or phosphate group, and a lipophilic residue. Dermatologically compatible anionic surfactants are known to the expert in large numbers from relevant manuals and are commercially available. More particularly, they are alkyl sulfates in the form of their alkali metal, ammonium or alkanolammonium salts, alkyl ether sulfates, alkyl ether carboxylates, acyl isethionates, acyl sarcosinates, acyl taurines with linear $C_{12-18}$ alkyl or acyl groups and sulfosuccinates and acyl glutamates in the form of their alkali metal or ammonium salts. According to the invention, particularly suitable anionic surfactants are, for example, Plantapon® CMGS (Sodium Hydrogenated Glyceryl Cocoate Sulfate), Plantapon® ACG 35 (Sodium Cocoyl Glutamate), Hostapon® CLG (Sodium Lauroyl Glutamate), Rewopol® SBCS 50K (Disodium PEG-5 Laurylcitrate Sulfosuccinate, Sodium Laureth Sulfate) and mixtures of these surfactants. Among the anionic surfactants, alkali metal salts of sulfosuccinates are particularly suitable for the preparations according to the invention because they are particularly kind to the skin and form very stable and intensive foams.

Zwitterionic surfactants are also particularly suitable for the purposes of the invention. Zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the INCI name of Cocamidopropyl Betaine is a particularly preferred zwitterionic surfactant. Tego® Betain 810 (INCI: Capryl/Capramidopropyl Betaine) and a surfactant mixture of Rewopol® SBCS 50 K (INCI: Disodium PEG-5 Laurylcitrate Sulfosuccinate, Sodium Laureth Sulfate) and Tego® Betain 810 (Capryl/Capramidopropyl Betaine), more particularly in a ratio by weight of 1:4 to 4:1 and preferably in a ratio by weight of 1:4 to 1:1, are particularly preferred for the purposes of the invention.

A particularly preferred embodiment of the sun protection emulsion contains (a) 2 to 10% by weight poly(12-hydroxystearic acid) polyglycerol ester, (b) 1 to 20% by weight oil components containing dialkyl carbonates, (c) 0.5 to 10% by weight of a mixture of Cocamidopropyl betaine and sulfosuccinates and (d) 0.5 to 20% by weight UV protection factors and (e) 30 to 80% by weight water.

Ampholytic surfactants are surface-active compounds which, in addition to a $C_{8/18}$ alkyl or acyl group, contain at least one free amino group and at least one —COOH or —$SO_3H$ group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Preferred ampholytic surfactants are N-cocoalkylaminopropionate, cocoacylaminoethyl aminopropionate and $C_{12/18}$ acyl sarcosine.

Particularly suitable cationic surfactants are quaternary ammonium compounds. Surfactants from this class have a particularly high affinity for the skin and can improve the degree of sensory smoothness. They include inter alia ammonium halides, more especially chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as for example the dialkyl ammonium methosulfates and methyl hydroxyalkyl dialkoyloxyalkyl ammonium methosulfates marketed under the name of Stepantex® and the corresponding products of the Dehyquart® series, may be used as cationic surfactants. "Esterquats" are generally understood to be quaternized fatty acid triethanolamine ester salts. They provide the compositions with particular softness. They are known substances which are prepared by the relevant methods of organic chemistry. Other cationic surfactants suitable for use in accordance with the invention are the quaternized protein hydrolyzates.

Nonionic Emulsifiers

The preparations according to the invention may additionally contain other nonionic emulsifiers which do not belong to the polyol poly-12-hydroxystearates mentioned as component (a). Nonionic emulsifiers are distinguished by their dermatological compatibility and mildness and by their favorable ecotoxicological properties. In addition, the stability and sensory profile of the compositions according to the invention can be improved by using a combination of nonionic w/o and o/w emulsifiers. The group of nonionic emulsifiers includes:

products of the addition of 2 to 50 mol ethylene oxide and/or 0 to 20 mol propylene oxide onto linear fatty alcohols containing 8 to 40 carbon atoms, onto fatty acids containing 12 to 40 carbon atoms and onto alkylphenols containing 8 to 15 carbon atoms in the alkyl group;

$C_{12/18}$ fatty acid monoesters and diesters of addition products of 1 to 50 mol ethylene oxide onto glycerol;

glycerol mono- and diesters and sorbitan mono- and diesters of saturated and unsaturated fatty acids containing 6 to 22 carbon atoms and ethylene oxide addition products thereof;

alkyl mono- and oligoglycosides containing 8 to 22 carbon atoms in the alkyl group and ethoxylated analogs thereof;

addition products of 7 to 60 mol ethylene oxide onto castor oil and/or hydrogenated castor oil;

other polyol esters and polyglycerol esters than those mentioned under component (a) such as, for example, polyglycerol diisostearate polyricinoleate or polyglycerol dimerate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6-22}$ fatty acids, ricinoleic acid and 12-hydroxystearic acid with pentaerythritol, dipentaerythritol, sugar alcohols (for example sorbitol), alkyl glucosides (for example methyl glucoside, butyl glucoside, lauryl glucoside) and polyglucosides (for example cellulose), or mixed esters such as, for example, glyceryl stearate citrate and glyceryl stearate lactate;

wool wax alcohols;

polysiloxane/polyalkyl/polyether copolymers and corresponding derivatives;

mixed esters of pentaerythritol, fatty acids, citric acid and fatty alcohol and/or mixed esters of fatty acids containing 6 to 22 carbon atoms, methyl glucose and polyols, preferably glycerol or polyglycerol, and polyalkylene glycols.

The addition products of ethylene oxide and/or propylene oxide onto fatty alcohols, fatty acids, alkylphenols, glycerol monoesters and diesters and sorbitan monoesters and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out. The emulsifiers are w/o or o/w emulsifiers according to the degree of ethoxylation. Reaction products with 1 to 100 mol ethylene oxide are particularly suitable for the preparations according to the invention.

Mixtures of polyol poly-12-hydroxystearates with other emulsifiers which are marketed by Cognis Deutschland GmbH & Co. KG under the name of Eumulgin® VL 75 (o/w emulsifier) and Dehymuls® SBL (w/o emulsifier) are preferred for the purposes of the invention.

In principle, suitable lipophilic w/o emulsifiers are emulsifiers with an HLB value of 1 to 8 which are listed in numerous Tables and are well-known to the expert. According to the invention, the HLB value for ethoxylated products may also be calculated to the following formula: HLB=(100-L): 5, where L is the percentage by weight of lipophilic groups, i.e. fatty alkyl or fatty acyl groups, in percent by weight in the ethylene oxide adducts.

Of particular advantage from the group of w/o emulsifiers are partial esters of polyols, more particularly $C_{3-6}$ polyols, such as for example glyceryl monoesters, partial esters of pentaerythritol or sugar esters, for example sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable emulsifiers.

The group of nonionic o/w emulsifiers (HLB value: 8-18) and/or solubilizers includes inter alia ethylene oxide adducts with a correspondingly high degree of ethoxylation, for example 10 to 20 ethoxylene oxide units for o/w emulsifiers and 20 to 40 ethylene oxide units for so-called solubilizers.

Nonionic emulsifiers from the group of alkyl oligoglycosides are particularly dermatologically compatible and, accordingly, may be particularly suitable o/w emulsifiers for the purposes of the invention because they have a particularly high stabilizing potential irrespective of the polarity of the oil component used, particularly in combination with the emulsifiers according to the invention. $C_{8-22}$ alkyl mono- and oligoglycosides, their production and their use are known from the prior art. They are produced in particular by reacting glucose or oligosaccharides with primary $C_{8-22}$, preferably $C_{12-22}$ and more particularly $C_{12-18}$ alcohols. So far as the glycoside unit is concerned, both monoglycosides where a cyclic sugar unit is attached to the fatty alcohol by a glycosidic linkage and oligomeric glycosides with a degree of oligomerization of preferably up to about 8 are suitable. The degree of oligomerization is a statistical mean value on which the homolog distribution typical of such technical products is based. Products available under the name of Plantacare® contain a $C_{8-16}$ alkyl group glucosidically linked to an oligoglucoside unit of which the average degree of oligomerization is 1 to 2. The acyl glucamides derived from glucamine are also suitable as nonionic emulsifiers. The 1:1 mixture of alkyl polyglucosides and fatty alcohols marketed by Cognis Deutschland GmbH & Co. KG under the name of Emulgade® PL 68/50 may advantageously be used for the purposes of the invention.

UV Protection Factors (Component d)

The sun protection emulsion contains a UV protection factor or a combination of UV protection factors as component (d). Combinations of different UV protection factors are preferred for the purposes of the invention because they guarantee "broad-band protection" against UV rays of various wavelengths.

According to the invention, suitable UV protection factors are organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP 0693471 B1;
  4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;
  esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);
  esters of salicylic acid, preferably salicylic acid-2-ethylhexyl ester, salicylic acid-4-isopropylbenzyl ester, salicylic acid homomenthyl ester;
  derivatives of benzophenone, preferably 2-hydroxy-4-methoxybenzophenone, 2-hydroxy-4-methoxy-4'-methylbenzophenone, 2,2'-dihydroxy-4-methoxybenzophenone;
  esters of benzalmalonic acid, preferably 4-methoxybenzalmalonic acid di-2-ethylhexyl ester;
  esters of benzalmalonic acid, preferably 4-methoxybenzalmalonic acid di-2-ethylhexyl ester;
  triazine derivatives such as, for example, 2,4,6-trianilino-(p-carbo-2'-ethyl-1'-hexyloxy)-1,3,5-triazine and Octyl Triazone, as described in EP 0818450 A1, or Dioctyl Butamido Triazone (Uvasorb® HEB);
  propane-1,3-diones such as, for example, 1-(4-tert.butylphenyl)-3-(4'-methoxyphenyl)-propane-1,3-dione;
  ketotricyclo(5.2.1.0)decane derivatives as described in EP 0694521 B1.

Suitable water-soluble substances are 2-phenylbenzimidazole-5-sulfonic acid and alkali metal, alkaline earth metal, ammonium, alkylammonium, alkanolammonium and glucammonium salts thereof;
  2,2-(1,4-phenylene)-bis-1H-benzimidazole-4,6-disulfonic acid and salts thereof, preferably the sodium salt;
  sulfonic acid derivatives of benzophenones, preferably 2-hydroxy-4-methoxybenzophenone-5-sulfonic acid and salts thereof;
  sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789), 1-phenyl-3-(4'-isopropylphenyl)-propane-1,3-dione and the enamine compounds described in DE 19712033 A1 (BASF). The UV-A and UV-B filters may of course also be used in the form of mixtures. Favorable combinations consist of the derivatives of benzoyl methane, for example 4-tert.butyl-4'-methoxydibenzoylmethane (Parsol® 1789) and 2-cyano-3,3-phenylcinnamic acid-2-ethylhexyl ester (Octocrylene) and Benzylidene Malonate Polysiloxane (Parsol® SLX), in combination with esters of cinnamic acid, preferably 4-methoxycinnamic acid-2-ethylhexyl ester and/or 4-methoxycinnamic acid propyl ester and/or 4-methoxycinnamic acid isoamyl ester. Parsol® SLX is a particularly suitable oil-soluble UV filter for the foam emulsions according to the invention with which the foam leaves the skin with a particularly good feeling. Combinations such as these are advantageously combined with water-soluble filters such as, for example, 2-phenylbenzimidazole-5-sulfonic acid and alkali metal, alkaline earth metal, ammonium, alkyl ammonium, alkanolammonium and glucammonium salts thereof. Ethylhexyl Triazone—Uvinul® T 150 (2,4,6-tris[p-(2-ethylhexyloxycarbonyl)anilino]-1,3,5-triazine, Diethylhexyl Butamido Triazone—Uvasorb® HEB (4,4'-[(6-[4-((1,1)-dimethylethyl)aminocarbonyl)phenylamino]-1,3,5-triazin-2,4-yl)-diiminio]bis-(benzoic acid-2-ethylhexyl ester, Octocrylene—

Neo Heliopan® 303 (2-cyano-3,3-diphenylacrylic acid-(2-ethylhexyl ester), Butyl Methoxydibenzoylmethane—Parsol®1789 (1-(4-tert.butylphenyl)-3-(4-methoxyphenyl)propane-1,3-dione, Ethylhexyl Methoxycinnamate—Neo Heliopan® AV (4-methoxycinnamic acid-2-ethylhexyl ester) or isoamyl-p-methoxycinamate Neo Heliopan® E 1000 (4-methoxycinnamic acid isoamyl ester), Homosalate—Neo Heliopan® HMS (3,3,5-trimethylcyclohexyl salicylate), Ethylhexyl Salicylate—Neo Heliopan® OS (salicylic acid-2-ethylhexyl ester), 4-Methylbenzylidene Camphor—Neo Heliopan® MBC (2-(4'-methylbenzylidene)-DL-campor, Phenylbenzimidazole Sulfonic Acid—Neo Heliopan® Hydro (2-phenylbenzimidazole-5-sulfonic acid and salts thereof), Disodium Phenyl Dibenzimidazole Tetrasulfonate—Neo Heliopan® AP (2,2-(1,4-phenylene)-bis-(1H-benzimidazole-4,6-disulfonic acid and salts thereof) are preferred for the purposes of the present invention.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments, for example micronized zinc oxide, are preferably used in sun protection products. Other suitable UV protection factors can be found in P. Finkel's overview in SÖFW Journal 122, 543 (1996) and in Parf. Kosm. 3, 11 (1999).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

A combination of primary UV protection factors or a combination of primary and secondary UV protection factors is preferably used in accordance with the invention,
Humectants/Skin Moisturizers In another preferred embodiment, the sun protection emulsion also contains a humectant which contributes towards optimizing the sensory properties of the composition and which serves to regulate the skin moisture level. At the same time, the low-temperature stability of the preparations according to the invention, particularly in the case of emulsions, is increased. The humectants are normally present in a quantity of 0.1 to 15% by weight, preferably 1 to 10% by weight and more particularly 3 to 5% by weight.

According to the invention, suitable humectants are inter alia amino acids, pyrrolidone carboxylic acid, lactic acid and salts thereof, lactitol, urea and urea derivatives, uric acid, glucosamine, creatinine, cleavage products of collagen, chitosan or chitosan salts/derivatives and, in particular, polyols and polyol derivatives (for example glycerol, diglycerol, triglycerol, ethylene glycol, propylene glycol, butylene glycol, erythritol, 1,2,6-hexanetriol, polyethylene glycols, such as PEG-4, PEG-6, PEG-7, PEG-8, PEG-9, PEG-10, PEG-12, PEG-14, PEG-16, PEG-18, PEG-20), sugars and sugar derivatives (inter alia fructose, glucose, maltose, maltitol, mannitol, inositol, sorbitol, sorbityl silanediol, sucrose, trehalose, xylose, xylitol, glucuronic acid and salts thereof), ethoxylated sorbitol (Sorbeth-6, Sorbeth-20, Sorbeth-30, Sorbeth-40), honey and hydrogenated honey, hydrogenated starch hydrolyzates and mixtures of hydrogenated wheat protein and PEG-20-acetate copolymer. According to the invention, particularly preferred humectants are glycerol, diglycerol and triglycerol.
Insect Repellents Another embodiment of the sun protection emulsion according to the invention may additionally contain insect repellents or a combination thereof.

Suitable insect repellents are, for example, N,N-diethylmtoluamide, pentane-1,2-diol, 3-(N-n-butyl-N-acetylamino)-propionic acid ethyl ester), which is marketed as Insect Repellent 3535 by Merck KGaA, and Butylacetylaminopropionate. They are normally used in the compositions according to the invention in a quantity of 0.1 to 10% by weight, preferably in a quantity of 1 to 8% by weight and more particularly in a quantity of 2 to 6% by weight, based on the overall composition.

Viscosity Adjusters

The required viscosity for the compositions according to the invention is achieved by addition of viscosity adjusters. Suitable viscosity adjusters are inter alia consistency factors such as, for example, fatty alcohols or hydroxyfatty alcohols containing 12 to 22 and preferably 16 to 18 carbon atoms and also partial glycerides, fatty acids containing 12 to 22 carbon atoms or 12-hydroxyfatty acids. A combination of these substances with alkyl oligoglucosides and/or fatty acid N-methyl glucamides of the same chain length is preferably used because combinations such as these provide particularly stable and homogeneous emulsions. Other suitable viscosity adjusters are thickeners such as, for example, Aerosil® types (hydrophilic silicas), polysaccharides, more especially xanthan gum, guarguar, agar-agar, alginates and tyloses, carboxymethyl cellulose and hydroxyethyl and hydroxypropyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), uncrosslinked and polyol-crosslinked polyacrylic acids, polyacrylamides, polyvinyl alcohol and polyvinyl pyrrolidone. Other viscosity adjusters which have proved to be particularly effective are bentonites, for example Bentone® Gel VS-5PC (Rheox) which is a mixture of cyclopentasiloxane, Disteardimonium Hectorite and propylene carbonate. Other suitable viscosity adjusters are surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable viscosity adjusters also include anionic, zwitterionic, amphoteric and nonionic copolymers such as, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, acrylamidopropyl trimethylammonium chloride/acrylate copolymers, octylacrylamide/methyl methacrylate/tert.-butylaminoethyl methacrylate/2-hydroxypropyl methacrylate copolymers, vinyl pyrrolidone/vinyl acetate copolymers, vinyl pyrrolidone/dimethylaminoethyl methacrylate/vinyl caprolactam terpolymers and optionally derivatized cellulose ethers and silicones.

Other Auxiliaries and Additives (Optional)

The compositions according to the invention may contain other auxiliaries and additives according to the particular application envisaged, including for example fats and waxes, pearlizing waxes, superfatting agents, stabilizers, cationic, zwitterionic or amphoteric polymers, biogenic agents, film formers, swelling agents, hydrotropes, preservatives, antidandruff agents, self-tanning agents, solubilizers, perfume oils, dyes, etc. which are mentioned by way of example in the following.

Fats and waxes in the context of the invention are understood to be any lipids of fat- or wax-like consistency which have a melting point above 20° C. These include, for example, the standard triacyl glycerols, i.e. the triple esters of fatty acids with glycerol which may be of vegetable or animal origin. They may also be mixed esters, i.e. triple esters of glycerol with various fatty acids, or mixtures of various glycerides, including mixtures of mono-, di- and triglycerides. So-called hardened fats and oils obtained by partial hydrogenation are also particularly suitable for the purposes of the invention. Vegetable hardened fats and oils are preferred, for example hardened castor oil, peanut oil, soybean oil, rape oil, rapeseed oil, cottonseed oil, sunflower oil, palm oil, palm kernel oil, linseed oil, almond oil, corn oil, olive oil, sesame oil, cocoa butter and coconut oil. Oxidation-stable vegetable glycerides commercially available as Cegesoft® and Novata® are particularly suitable.

Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Besides the fats, other suitable additives are fat-like substances, such as lecithins and phospholipids. Lecithins are glycerophospholipids which are formed from fatty acids, glycerol, phosphoric acid and choline by esterification and are also frequently referred to as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates). Sphingosines and sphingolipids are also suitable as fat-like substances.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially Lauron®; distearylether; fatty acids, such as stearic acid, $C_{12-22}$ hydroxyfatty acids, behenic acid, ring opening products of $C_{12-22}$ olefin epoxides with $C_{12-22}$ fatty alcohols and/or polyols containing 2 to 15 carbon atoms and 2 to 10 hydroxyl groups and mixtures thereof.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Metal salts of fatty acids such as, for example, magnesium, aluminium and/or zinc stearate or ricinoleate may be used as stabilizers.

Suitable cationic polymers, which further optimize the sensory profile of the compositions according to the invention and give the skin a feeling of softness, are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable silicone compounds were mentioned above in connection with the oil components. Besides dimethyl polysiloxanes, methylphenyl polysiloxanes and cyclic silicones, other suitable silicone compounds are amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and silicon dioxide or hydrogenated silicates.

Biogenic agents suitable for the purposes of the invention are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes. Active components such as these are used as radical traps in sun protection formulations and serve to regenerate the skin.

So-called film formers, which lead to a further improvement in the sensory profile of the preparations according to the invention, are, for example, chitosan, microcrystalline chitosan, quaternized chitosan, collagen, hyaluronic acid and salts thereof and similar compounds and the polyvinyl pyrrolidones, vinyl pyrrolidone/vinyl acetate copolymers, polymers of the acrylic acid series and quaternary cellulose derivatives.

Suitable antidandruff agents are Piroctou Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

A suitable self-tanning agent is, for example, dihydroxyacetone. Suitable tyrosinase inhibitors, which prevent the formation of melanin and are used in depigmenting agents, are, for example, arbutin, ferulic acid, koji acid, coumaric acid and ascorbic acid (vitamin C).

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

short-chain alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetik-verordnung ("Cosmetics Directive").

Suitable perfume oils are natural, vegetable and animal and also synthetic perfumes or mixtures thereof. Natural perfumes are obtained inter alia by extraction of flowers, stems and leaves, fruits, fruit peel, roots and resins of plants. Animal raw materials, for example civet and beaver, may also be used. Typical synthetic perfume compounds are products of the ester, ether, aldehyde, ketone, alcohol and hydrocarbon type. Mixtures of various perfumes, which together produce an attractive perfume note, are preferably used.

Suitable dyes are any of the substances suitable and approved for cosmetic purposes The Foam Dispenser The sun protection emulsions may be foamed from a dispenser either with air or with a blowing gas. Foam dispensers known per se may be used to foam the sun protection emulsion; dispensers based on a blowing gas or mechanical foam dispensers with a pump mechanism for foaming the sun protection emulsion with air may be used.

One embodiment of the invention contains the sun protection emulsion together with a blowing gas in a foam dispenser operating on the basis of a blowing gas. The blowing gas is preferably accommodated in compressed form together with the sun protection emulsion in a pressurized container with a spray head. Any commercially available blowing gas mixtures may be used for this purpose. Hydrocarbon-containing blowing gases and blowing gas mixtures can be particularly suitable, the presence of $C_5$ alkanes leading to a so-called post-foaming effect. Suitable blowing gases of the type in question are, for example, n-pentane, 2-methylbutane (=isopentane) and neopentane, 2-methylbutane being particularly suitable for producing a post-foaming effect. Other suitable blowing gas mixtures are mixtures of $C_4$ alkanes and $C_5$ alkanes and fluorinated analogs thereof.

In a particularly preferred embodiment, however, the sun protection emulsion is accommodated in a foam dispenser comprising a pump mechanism for foaming with air. A foam dispenser such as this eliminates the need for large amounts of volatile organic blowing gas precursors. This is particularly advantageous because sun protection preparations are often exposed to direct sunlight and become heated in use, for example during sunbathing on the beach.

The foam dispenser to be used is intended to enable the user readily to produce a particularly intensive and stable foam, which does not collapse and is therefore easy to spread, from the sun protection emulsion according to the invention in a simple and very safe manner.

This requirement is satisfied by a foam dispenser with the features described below. This dispenser may be, for example, a foam dispenser constructed similarly to the dispenser known from WO 00/78629 A1 (Airspray N.V.) which is marketed under the name of F2 Finger Pump Foamer®.

The mixing ratio of air to liquid during production of the foam is particularly important for producing a foam with the properties mentioned above. To this end, it is proposed that the air to liquid mixing ratio in the dispenser should be 5:1 to 30:1, preferably 8:1 to 20:1 and more particularly ca. 10:1.

With the use of the foam dispenser filled with the sun protection emulsion according to the invention in mind, a particularly suitable shot volume of the foam dispenser is 0.1 to 1 ml, preferably 0.2 to 0.5 ml and, more particularly, ca. 0.4 ml liquid per shot. The amount of foam thus dispensed can be spread by one hand over a sufficiently large area of skin on the one hand without the foam volume being too large and unmanageable or, on the other hand, without the foam dispenser having to be actuated too often.

For effectively producing a foam with the properties mentioned above, it has also proved to be of advantage for the foam dispenser to comprise an outlet passage with a foam generator comprising at least one and preferably at least two flat sieves arranged in tandem which are disposed in and substantially transversely of the outlet passage. In this foam generator, the mixture of air and liquid is forced through sieves and the foam is produced in this way.

In order to guarantee the air to liquid mixing ratio so important for foam production, even under adverse ambient conditions, it is of advantage to avoid the penetration of liquid, for example water, from outside into the air pump chamber of the foam dispenser. To this end, the foam dispenser has at least one air inlet into an air pump chamber which is protected against the penetration of liquid, especially water, by a removable protective cap. This is because, if water that has entered the air pump chamber is foamed together with the sun protection emulsion and the air, the intended air to liquid mixing ratio is undesirably altered, so that the quality of the foam produced can be expected to deteriorate.

However, should water already have penetrated into the air pump chamber, the preferred air to liquid mixing ratio can still readily be maintained if, as in another preferred embodiment, the air pump chamber has a minimum volume different from zero. Any penetrating water is able to collect in this minimum volume, which may also be referred to as a residual volume, so that, when the foam dispenser is actuated, this water is not foamed together with the sun protection emulsion, but stays in the air pump chamber.

EXAMPLES

The preparations according to the invention were produced by standard cold or hot processes. The fatty phase and water phase (without surfactants) were heated to ca. 80° C. and combined while stirring. The combined phases were then cooled while stirring to ca. 40° C. and the surfactants were added. After the perfumes had been added at 25° C., the emulsion was homogenized.

The quantities mentioned in the following Examples are based on % by weight of the commercially available substance of the stored sun protection emulsion, unless otherwise indicated. Examples 1 to 4 are formulations corresponding to the invention; Example C1 is a Comparison Example. The INCI nomenclature is shown in brackets.

Sun Protection Emulsion

Example 1

| | |
|---|---|
| Dehymuls ® PGPH (Polyglyceryl-2 Dipolyhydroxystearate) | 4.00% by wt. |
| Cetiol ® CC (Dicaprylyl Carbonate) | 5.00% by wt. |
| Myritol ® 312 (Caprylic/Capric Triglyceride) | 3.00% by wt. |
| Neo Heliopan ® MBC (4-Methylbenzylidene Camphor) | 4.00% by wt. |
| Neo Heliopan ® OS (Ethylhexyl Salicylate) | 2.00% by wt. |
| Parsol ® 1789 (Butyl Methoxydibenzoylmethane) | 2.00% by wt. |
| Copherol ® 1250 (Tocopheryl Acetate) | 0.60% by wt. |
| Stay-C ® 50 (Sodium Ascorbyl Phosphate) | 0.10% by wt. |
| Neo Heliopan ® Hydro (Phenylbenzimidazole Sulfonic Acid) | 1.00% by wt. |
| Sodium hydroxide | 0.20% by wt. |
| Rewopol ® SB CS 50K (Disodium PEG-5 Laurylcitrate Sulfosuccinate. Sodium Laureth Sulfate) | 2.00% by wt. |
| Tego ® Betain 810 (Capryl/Capramidopropyl Betaine) | 3.00% by wt. |
| Preservative | q.s. |
| Perfume | q.s. |
| Water | to 100% by wt. |

Sun Protection Emulsion

Example 2

| | |
|---|---|
| Dehymuls ® PGPH (Polyglyceryl-2 Dipolyhydroxystearate) | 4.00% by wt. |
| Cetiol ® CC (Dicaprylyl Carbonate) | 5.00% by wt. |
| Myritol ® 331 (Cocoglycerides) | 3.00% by wt. |
| Neo Heliopan ® MBC (4-Methylbenzylidene Camphor) | 4.00% by wt. |
| Neo Heliopan ® OS (Ethylhexyl Salicylate) | 2.00% by wt. |
| Uvasorb ® HEB (Diethylhexyl Butamido Triazone) | 3.00% by wt. |
| Parsol ® 1789 (Butyl Methoxydibenzoylmethane) | 2.00% by wt. |
| Copherol ® 1250 (Tocopheryl Acetate) | 0.60% by wt. |
| Stay-C ® 50 (Sodium Ascorbyl Phosphate) | 0.10% by wt. |
| Neo Heliopan ® Hydro (Phenylbenzimidazole Sulfonic Acid) | 1.00% by wt. |
| Sodium hydroxide | 0.20% by wt. |
| Rewopol ® SB CS 50K (Disodium PEG-5 Laurylcitrate Sulfosuccinate. Sodium Laureth Sulfate) | 2.00% by wt. |
| Tego ® Betain 810 (Capryl/Capramidopropyl Betaine) | 3.00% by wt. |
| Preservative | q.s. |
| Perfume | q.s. |
| Water | to 100% by wt. |

Sun Protection Emulsion

Example 3

| | |
|---|---|
| Dehymuls ® PGPH (Polyglyceryl-2 Dipolyhydroxystearate) | 4.00% by wt. |
| Cetiol ® CC (Dicaprylyl Carbonate) | 5.00% by wt. |
| Myritol ® 331 (Cocoglycerides) | 3.00% by wt. |
| Neo Heliopan ® MBC (4-Methylbenzylidene Camphor) | 4.00% by wt. |
| Parsol ® SLX (Benzylidene Malonate Polysiloxane) | 2.00% by wt. |
| Uvasorb ® HEB (Diethylhexyl Butamido Triazone) | 3.00% by wt. |
| Parsol ® 1789 (Butyl Methoxydibenzoylmethane) | 2.00% by wt. |
| Copherol ® 1250 (Tocopheryl Acetate) | 0.60% by wt. |
| Stay-C ® 50 (Sodium Ascorbyl Phosphate) | 0.10% by wt. |
| Neo Heliopan ® Hydro (Phenylbenzimidazole Sulfonic Acid) | 1.00% by wt. |

-continued

| | |
|---|---|
| Sodium hydroxide | 0.20% by wt. |
| Rewopol ® SB CS 50K | 2.00% by wt. |
| (Disodium PEG-5 Laurylcitrate Sulfosuccinate. | |
| Sodium Laureth Sulfate) | |
| Tego ® Betain 810 (Capryl/Capramidopropyl Betaine) | 3.00% by wt. |
| Preservative | q.s. |
| Perfume | q.s. |
| Water | to 100% by wt. |

Sun Protection Emulsion

Example 4

| | |
|---|---|
| Dehymuls ® PGPH | 4.00% by wt. |
| (Polyglyceryl-2 Dipolyhydroxystearate) | |
| Cetiol ® OE (Dicaprylyl Ether) | 2.00% by wt. |
| Finsolv ® TN (C12/15 Alkyl Benzoate) | 3.00% by wt. |
| Cegesoft ® C 24 (Ethylhexyl Palmitate) | 3.00% by wt. |
| Neo Heliopan ® MBC (4-Methylbenzylidene Camphor) | 4.00% by wt. |
| Neo Heliopan ® OS (Ethylhexyl Salicylate) | 2.00% by wt. |
| Neo Heliopan ® AP | 3.00% by wt. |
| (Disodium Phenyl Dibenzimidazole Tetrasulfonate) | |
| Copherol ® 1250 (Tocopheryl Acetate) | 0.60% by wt. |
| Stay-C ® 50 (Sodium Ascorbyl Phosphate) | 0.10% by wt. |
| Neo Heliopan ® Hydro | 1.00% by wt. |
| (Phenylbenzimidazole Sulfonic Acid) | |
| Sodium hydroxide | 0.20% by wt. |
| Rewopol ® SB CS 50K | 2.00% by wt. |
| (Disodium PEG-5 Laurylcitrate Sulfosuccinate. | |
| Sodium Laureth Sulfate) | |
| Tego ® Betain 810 (Capryl/Capramidopropyl Betaine) | 3.00% by wt. |
| Glycerin | 3.00% by wt. |
| Preservative | q.s. |
| Perfume | q.s. |
| Water | to 100% by wt. |

Sun Protection Emulsion

Comparison Example (Non-Foamable)

| | |
|---|---|
| Rylo ® PG 19 (Polyglyceryl-3 Polyricinoleate) | 4.00% by wt. |
| Cetiol ® CC (Dicaprylyl Carbonate) | 5.00% by wt. |
| Myritol ® 331 (Cocoglycerides) | 3.00% by wt. |
| Neo Heliopan ® MBC (4-Methylbenzylidene Camphor) | 4.00% by wt. |
| Neo Heliopan ® OS (Ethylhexyl Salicylate) | 2.00% by wt. |
| Uvasorb ® HEB (Diethylhexyl Butamido Triazone) | 3.00% by wt. |
| Parsol ® 1789 (Butyl Methoxydibenzoylmethane) | 2.00% by wt. |
| Copherol ® 1250 (Tocopheryl Acetate) | 0.60% by wt. |
| Stay-C ® 50 (Sodium Ascorbyl Phosphate) | 0.10% by wt. |
| Neo Heliopan ® Hydro | 1.00% by wt. |
| (Phenylbenzimidazole Sulfonic Acid) | |
| Sodium hydroxide | 0.20% by wt. |
| Rewopol ® SB CS 50K | 2.00% by wt. |
| (Disodium PEG-5 Laurylcitrate Sulfosuccinate. | |
| Sodium Laureth Sulfate) | |
| Tego ® Betain 810 (Capryl/Capramidopropyl Betaine) | 3.00% by wt. |
| Preservative | q.s. |
| Perfume | q.s. |
| Water | to 100% by wt. |

Example Foam Dispenser (FIG. 1):

The sole drawing is a longitudinal section through a foam dispenser with an Airspray International B.V. pump mechanism which is particularly suitable for foaming and dosing the sun protection emulsion according to the invention, The drawing shows the foam dispenser without the liquid container designed to be screwed on from below and in a position before actuation of the pump mechanism. In the assembled state, the liquid container, of which the mouth has an external screwthread, is screwed into the internal screwthread 1 of the foam pump 2 shown in FIG. 1. Accordingly, the foam dispenser consists of the foam pump 2 and the liquid container (not shown) for the sun protection emulsion.

Figure 1:
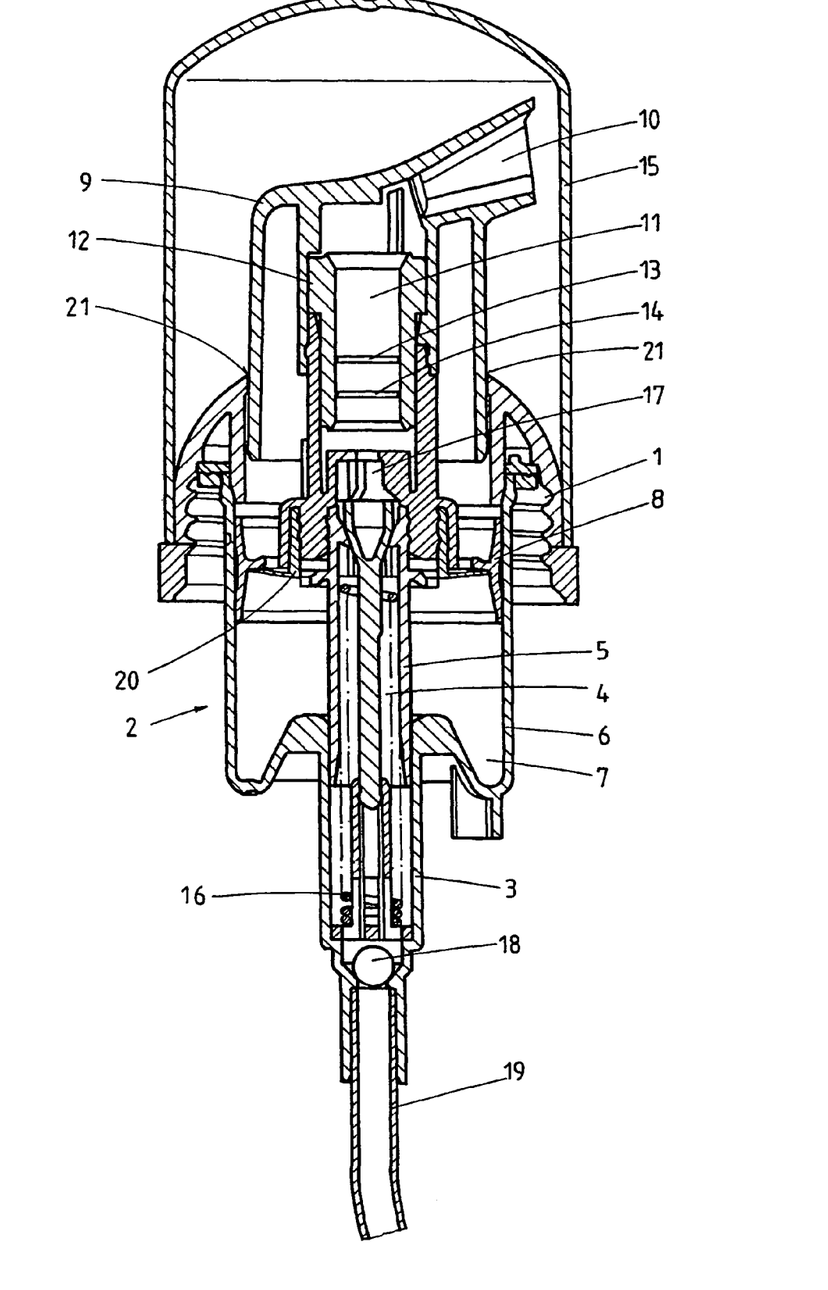
The FIGURE is a cross-sectional view of an air-injecting foam dispenser head.

The foam pump 2 contains a liquid pump 3 with a pump chamber 4 and a pump piston 5 for the liquid. In addition, an air pump 6 is provided with an air pump chamber 7 and an air pump piston 8. The two pistons, i.e. the liquid pump piston 5 and the air pump piston 8 are mechanically connected to an operating head 9.

The operating head 9 has an outlet opening 10 directed obliquely upwards for the foam and an outlet passage 11 extending longitudinally of the foam dispenser, i.e. perpendicularly in FIG. 1, in which a foam generator 12 is disposed. The foam generator 12 consists of a sleeve with two flat sieves 13, 14 inserted transversely of the longitudinal axis. Finally, the operating head 9 is surrounded by a removable protective cap 15.

The other key components of this foam dispenser are explained in the following in the description of the mode of operation. For actuation, the user removes the protective cap 15 and presses down on the operating head 9 so that the operating head 9 moves downwards against the force of a compression spring 16. At the same time, the pump piston 5 for the liquid and the air pump piston 8 slide downwards in their respective pump chambers 4 and 7, so that the particular volumes of the corresponding pump chambers 4, 7 are reduced and both air and liquid pass into a mixing chamber 17 in which air and liquid are mixed. The mixture then flows through the flat sieves 13 and 14, producing a foam which is then dispensed outwards through the outlet passage 11 and the outlet opening 10.

After the foam has been dispensed, the user releases the operating head 9 which then returns to its starting position shown in FIG. 1 under the force of the compression spring 16. This return movement is accompanied by the opening of a nonreturn valve 18, of which the valve element is in the form of a ball, and the pump chamber 4 for the liquid is filled with the sun protection emulsion which is taken in by suction from the liquid container (not shown in FIG. 1) via a small tube 19. At the same time, a flexible annular valve seal 20 of the air pump chamber 7 opens to take air into the air pump chamber 7 from outside through an air inlet 21.

When the operating head 9 has reached its upper position as shown in FIG. 1, the foam dispenser is able to produce and re-dispense foam-like sun protection emulsion by depression of the operating head 9. During the depression of the operating head, the nonreturn valve 18 for the inlet of the liquid pump chamber 4 and the valve seal 20 for the air pump chamber 7 close, so that the liquid and the air are only able to pass into the mixing chamber 17 through predetermined passages.

In this preferred embodiment, the liquid to air mixing ratio in the pump so important to production of the foam is ca. 10:1. With each actuation, ca. 0.4 ml liquid is dispensed in the form of foam. One such pump is commercially available under the name of M3 from Airspray International B.V., Alkmaar, Netherlands.

In order to guarantee the above-mentioned mixing ratio between air and sun protection emulsion under all ambient conditions, it is also of advantage for the air inlet 21 into the air pump chamber 7 to be well protected against the penetration of liquid, for example water, from outside. This is because, if water should enter the air pump chamber 7, it could be forced together with the air into the mixing chamber 17, so that the air to liquid mixing ratio would be undesirably altered and the quality of the foam produced would be reduced.

The protective cap 15 affords some protection against the penetration of water when the foam dispenser is not in use. In the case of the pump in the illustrated embodiment, further protection against any deterioration in the mixing ratio by water penetrating into the air pump chamber 7 is also provided by the fact that the end of the air pump piston 8 and the shape of the base of the air pump chamber 7 do not correspond. Thus, when the actuating head 9 is fully depressed, a certain residual volume (minimum volume) always remains in the air pump chamber 7 which, in the illustrated embodiment, is in the form of an annular space in which any penetrating water is able to collect without being transported together with the air into the mixing chamber 17.

| List of Reference Numerals | |
|---|---|
| 1 | internal screwthread |
| 2 | foam pump |
| 3 | liquid pump |
| 4 | pump chamber for liquid |
| 5 | pump piston for liquid |
| 6 | air pump |
| 7 | air pump chamber |
| 8 | air pump piston |
| 9 | operating head |
| 10 | outlet opening |
| 11 | outlet passage |
| 12 | foam generator |
| 13 | flat sieve |
| 14 | flat sieve |
| 15 | protective cap |
| 16 | compression spring |
| 17 | mixing chamber |
| 18 | nonreturn valve |
| 19 | small tube |
| 20 | valve seal |
| 21 | air inlet |

APPENDIX

1) Cegesoft® C 24
   INCI: Ethylhexyl Palpitate
   Manufacturer: Cognis Deutschland GmbH & Co. KG
2) Cetiol®CC
   INCI: Dicaprylyl Carbonate
   Manufacturer: Cognis Deutschland GmbH & Co. KG
3) Copherol® 1250
   INCI: Tocopheryl Acetate
   Manufacturer: Cognis Corporation
4) Dehymuls® PGPH
   INCI: Polyglyceryl-2 Dipolyhydroxystearate
   Manufacturer: Cognis Deutschland GmbH & Co. KG
5) Finsolv® TN
   INCI: C12/15 Alkyl Benzoate
   Manufacturer: Nordmann Rassmann
6) Myritol® 312
   INCI: Caprylic/Capric Triglyceride
   Manufacturer: Cognis Deutschland GmbH & Co. KG
7) Myritol® 331
   INCI: Cocoglycerides
   Manufacturer: Cognis Deutschland GmbH & Co. KG
8) Neo Heliopan® AP
   INCI: Disodium Phenyl Dibenzimidazole Tetrasulfonate
   Manufacturer: Haarmann & Reimer
9) Neo Heliopan® MBC
   INCI: 4-Methylbenzylidene Camphor
   Manufacturer: Haarmann & Reimer
10) Neo Heliopan® OS
    INCI: Ethylhexyl Salicylate
    Manufacturer: Haarmann & Reimer
11) Neo Heliopan® Hydro
    INCI: Phenylbenzimidazole Sulfonic Acid
    Manufacturer: Haarmann & Reimer
12) Parsol® 1789
    INCI: Butyl Methoxydibenzoylmethane
    Manufacturer: Hoffmann-La Roche (Givaudan)
13) Parsol® SLX
    Benzylidene Malonate Polysiloxane
    Manufacturer: Hoffmann-La Roche
14) Rylo® PG 19
    INCI: Polyglyceryl-3 Polyricinoleate
    Manufacturer: Danisco Cultor
15) Rewopol® SB CS 50K
    INCI: Disodium PEG-5 Laurylcitrate Sulfosuccinate, Sodium Laureth Sulfate
    Manufacturer: Goldschmidt-Rewo
16) Stay-C® 50
    INCI: Sodium Ascorbyl Phosphate
    Manufacturer: Hoffmann-La Roche
17) Tego® Betain 810
    INCI: Capryl/Capramidopropyl Betaine
    Manufacturer: Goldschmidt-Rewo
18) Uvasorb® HEB
    INCI: Diethylhexyl Butamido Triazone
    Manufacturer: Sigma

We claim:

1. A foam-producing and dispensing system for dispensing a sun protection emulsion in the form of a foam, comprising: a manually-operated foam dispenser containing a foamable, sun protection water-in-oil emulsion, comprising:
   (a) at least one polyol poly-12-hydroxystearate;
   (b) an oil component;
   (c) at least one surfactant selected from the group consisting of anionic surfactants, zwitterionic surfactants, and mixtures thereof;
   (d) a UV protection factor; and
   (e) water,
   wherein component (a) enhances the foamability of said emulsion, and wherein said emulsion forms a foam when dispensed.

2. The system as claimed in claim 1 wherein the sun protection emulsion comprises:
   (a) 2 to 10% by weight of at least one polyol poly-12-hydroxystearate;
   (b) 1 to 20% by weight of an oil component;
   (c) 0.5 to 10% by weight of at least one surfactant;
   (d) 0.5 to 20% by weight of a UV protection factor; and
   (e) 30 to 80% by weight water.

3. The system as claimed in claim 1, wherein the at least one polyol poly-12-hydroxystearate (a) comprises poly(12-hydroxystearic acid) polyglycerol ester.

4. The system as claimed in claim 1, wherein the sun protection emulsion comprises:
   (a) 2 to 10% by weight of at least one poly(12-hydroxystearic acid) polyglycerol ester;
   (b) 1 to 20% by weight of at least one oil component comprising a dialkyl carbonate;
   (c) 0.5 to 10% by weight of a mixture of Cocamidopropylbetaine and a sulfosuccinate;
   (d) 0.5 to 20% by weight of a sun protection factor; and
   (f) 30 to 80% by weight water.

5. The system as claimed in claim 1, wherein the sun protection emulsion is dispensed with a gas in compressed form in a foam dispenser.

6. The system as claimed in claim 1, wherein the sun protection emulsion is dispensed in a foam dispenser comprising a pump mechanism for combining the emulsion with air to form and dispense a foam.

7. The system as claimed in claim 6, wherein the foam dispenser has an air to liquid mixing ratio of from 5:1 to 30:1.

8. The system as claimed in claim 6, wherein the foam dispenser has a shot volume of from 0.1 to 1 ml liquid per shot.

9. The system as claimed in claim 6, wherein the foam dispenser has an outlet passage with a foam generator comprising at least one flat sieve arranged in and substantially transverse to the outlet passage.

10. The system as claimed in claim 6, wherein the foam dispenser has at least one air inlet into an air pump chamber and the air inlet is protected against the penetration of liquid by a removable protective cap.

11. The system as claimed in claim 6, wherein the foam dispenser comprises an air pump chamber having a residual volume for collecting residual liquid.

* * * * *